(12) United States Patent  
Owen et al.

(10) Patent No.: US 8,083,913 B2  
(45) Date of Patent: Dec. 27, 2011

(54) ELECTROCHEMICAL CELL FOR TESTING THE ELECTROCATALYTIC BEHAVIOR OF MULTIPLE MATERIALS

(75) Inventors: John Robert Owen, Southampton (GB); Philip Nigel Bartlett, Alresford (GB); Brian Elliot Hayden, Southampton (GB); Andrea Elizabeth Russell, Warminster (GB); Karen Marie Brace, Southampton (GB)

(73) Assignee: University of Southampton, Southampton (GB)

( * ) Notice: Subject to any disclaimer, the term of this patent is extended or adjusted under 35 U.S.C. 154(b) by 1095 days.

(21) Appl. No.: 10/541,511

(22) PCT Filed: Jan. 9, 2004

(86) PCT No.: PCT/GB2004/000085

§ 371 (c)(1), (2), (4) Date: Mar. 2, 2006

(87) PCT Pub. No.: WO2004/063742

PCT Pub. Date: Jul. 29, 2004

(65) Prior Publication Data

US 2007/0056851 A1    Mar. 15, 2007

(30) Foreign Application Priority Data

Jan. 10, 2003  (GB) .................................. 0300558.4

(51) Int. Cl.  
*G02F 1/163*  (2006.01)  
*G01N 27/407*  (2006.01)

(52) U.S. Cl. .......... 204/424; 204/400; 359/265
(58) Field of Classification Search .......... 359/265  
See application file for complete search history.

(56) References Cited

U.S. PATENT DOCUMENTS

2003/0066519 A1 * 4/2003 Wachsman et al. .......... 123/703

OTHER PUBLICATIONS

English translation of Abstract of Japan Patent No. 6160344.*  
Sullivan et al, Analytical Chemistry, Oct. 1999, 71(19), p. 4369-4375.*  
Kudla, R. J., S. Subramanian, M. S. Chattha, and T. E. Hoost. "Effect of Tungsten Oxide Addition on the Catalytic Activity of Gamma-Al2O3 for NOx Reduction from Fuel-Lean Gas Mixtures." Ind. Eng. Chem. Res. 35 (1996): 4394-397.*

* cited by examiner

*Primary Examiner* — Kaj K Olsen  
*Assistant Examiner* — Kourtney R Salzman  
(74) *Attorney, Agent, or Firm* — Pearl Cohen Zedek Latzer, LLP (57) ABSTRACT

An electrochemical cell for testing the electrochemical behavior of a plurality of materials comprises: a first electrode; a counter-electrode bearing an electrochromic material having a visual or measurable property which changes in a manner proportional to the total charge passed through it; and an electrolyte between and in electrical contact with the first electrode and the counter-electrode; wherein one of the first electrode and the electrolyte comprises a plurality of regions, each region comprising a sample of material to be tested, the regions being, in the case of the first electrode, electrically connected to a common terminal. Such a cell can be used for a "combinatorial chemistry" approach to testing the properties of possible cell components.

4 Claims, 7 Drawing Sheets

ELECTROCHEMICAL CELL FOR TESTING THE ELECTROCATALYTIC BEHAVIOR OF MULTIPLE MATERIALS

CROSS-REFERENCE TO RELATED APPLICATIONS

This application is a National Phase Application of PCT International Application No. PCT/GB2004/000085, International Filing Date 9 Jan. 2004, claiming priority of UK Patent Application GB 0300558.4, filed 10 Jan. 2003, each of which are hereby incorporated by reference in their entirety.

FIELD OF THE INVENTION

The present invention relates to a method of testing materials for electrochemical uses, especially for use as electrocatalysts, and more particularly as electrocatalysts for use in fuel cells, such as methanol fuel cells.

BACKGROUND OF THE INVENTION

There has been increasing interest in recent years in fuel cells, i.e. electrochemical cells which produce electricity directly from the oxidation of a fuel, such as methanol. These cells require catalysts and their efficiency is directly related to the activity of the catalysts employed. However, minor differences in a catalyst formulation can have a major effect upon the activity of that material as a catalyst, and, since there are many variables even in a simple catalyst, testing a multitude of individual materials for their activity as catalysts is time-consuming and expensive. In addition, transmission of information from a large array of cells requires many wire connections to the cells and many wires to transmit signals between the cells and the monitoring equipment.

A paper entitled "Detection of Catalytic Activity in Combinatorial Libraries of Heterogeneous Catalysts by IR Thermography" [Angew. Chem., Int. Ed. (1998), 37, 2644-7], A. Holzwarth et al., describes the measurement of catalyst activity by measuring temperature change across an array of catalysts exposed to reducing gases mixed with oxygen. Although this technique does not require wire connections and can give a general indication of the chemical activity in oxygen, the results do not apply directly to electrochemical cells where oxygen gas does not make direct contact with the reactant.

In another paper entitled "Automated Electrochemical Combinatorial Electrode Arrays" [Anal. Chem. (1999), 71, 4369-4375], M. G. Sullivan et al. propose the use of a technique based upon the principles of combinatorial chemistry to solve this problem. The proposed technique involves the use of a test electrochemical cell in which one electrode is based upon a structured array of the materials to be tested for their activity as electrocatalysts and the electrolyte is a special electrolyte composition which, due to the electrocatalysis, fluoresces to an extent proportional to the current passed. Whilst this does, indeed, allow for many materials to be tested rapidly and economically, the method interferes with the chemical environment of the electrocatalyst by adding and/or substituting components to the electrolyte solution which are not normally present in the fuel cell. Therefore, the results obtained using such a test cell may not be truly representative of what would be obtained if the same electrocatalysts were used in a fuel cell containing only the desired fuel dissolved in the specified electrolyte.

Finally, a paper entitled "High Throughput Screening System for Catalytic Hydrogen-Producing Materials" [J. Comb. Chem. (2002), 4, 17-22], T. F. Jaramillo et al., describes the use of a Pd-coated tungsten oxide film in a colourimetric method to detect electrolytically generated hydrogen gas from an array of electrocatalysts. In this case the catalytic reaction examined is quite different from the reaction required of a fuel cell electrocatalyst.

SUMMARY OF THE INVENTION

The present invention allows the simultaneous examination of a large number of candidate electrocatalysts while exposed to exactly the same electrolyte and fuel that would be anticipated to be used in the fuel cell. Thus, the method of the present invention, while still benefiting from the advantages of the combinatorial chemistry-like approach, also overcomes the disadvantages of the previous proposals.

In accordance with the present invention, there is provided an electrochemical cell for testing the electrochemical behaviour of a plurality of materials, said cell comprising:
a first electrode;
a counterelectrode bearing an electrochromic material whose reflection, refraction or absorption of electromagnetic energy (such as ultraviolet, visible, infrared, or microwave radiation), changes in a manner proportional to the total charge passed through it; and
an electrolyte between and in electrical contact with the first electrode and the counterelectrode;
wherein one of said first electrode and said electrolyte comprises a plurality of regions, each region comprising a sample of material to be tested, the regions being, in the case of the first electrode, electrically connected to a common terminal.

A reference electrode may also be contacted with the electrolyte for potential measurement and control. Alternatively, the counterelectrode may be used for these purposes.

In one embodiment of the present invention, the first electrode comprises a plurality of regions of the material to be tested. In this case, the material being tested may be an electrocatalyst, a battery electrode material (e.g. $MnO_2$), or a hydrogen storage alloy. In this case, the electrolyte will be chosen having regard to the intended use of the test material, as described in more detail below.

In a second embodiment of the present invention, the electrolyte comprises a plurality of regions of the material to be tested. In this case, the first electrode will be chosen having regard to the intended use of the test material, as described in more detail below.
with the following:

BRIEF DESCRIPTION OF THE DRAWINGS

The invention is illustrated by the following non-limiting examples with reference to the Figures, in which.

DETAILED DESCRIPTION OF THE INVENTION

When an electrical current is caused to flow between the first electrode and the imaging counterelectrode by connecting to an external measuring instrument, such as a potentiostat, a visual or measurable property of the electrochromic material closest to (and normally opposite to) each region of the first electrode or each region of the electrolyte will change (for example, the colour, intensity of colour or other property) in proportion to the total charge passed during the test period through that region containing the material under test. If each of the test regions is made up of a different material, e.g. for use as an electrocatalyst, the electrochemical behaviour, e.g. catalytic activity, of each material will determine the charge passed and so the colour or other property of the electrochromic material. The absolute values of the charges and the corresponding currents may be obtained from a calibration of the electrochromic material under galvanostatic conditions. The imaging counterelectrode can also act as a reference electrode provided account is taken of its potential/charge relation as measured during the preparation of the calibration sample. Thus, the potential at the working electrode is computed by subtracting the requisite reference potential from the scanned potential at each point.

Figure 1:
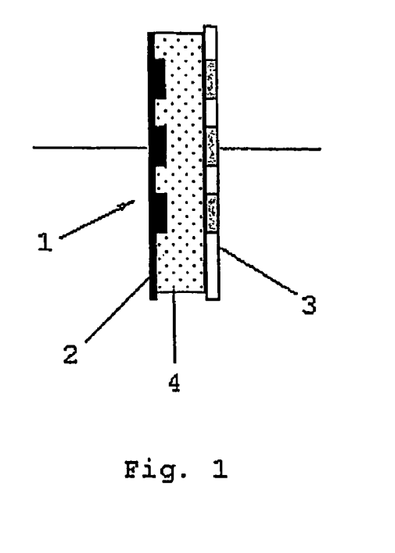
FIG. 1 is a simplified side view of the two electrodes in a test cell in accordance with one embodiment of the present invention.
Figure 2:
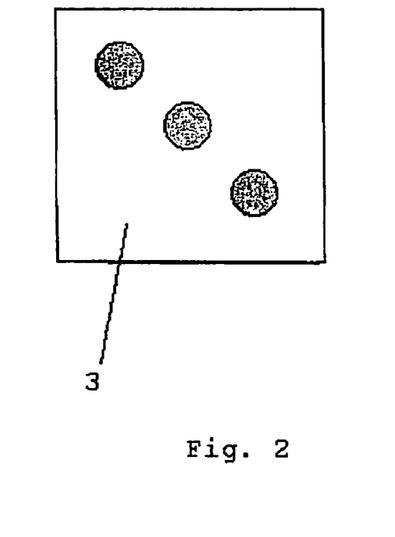
FIG. 2 shows the simplified counter-electrode of FIG. 1.

Accordingly, as shown in FIGS. 1 and 2 of the accompanying drawings, the principle of the imaging counterelectrode employed in the present invention is that certain electrode materials, namely electrochromic materials such as tungsten oxide, change colour in response to the charge passed. Thus the charge passed at a given position on a planar electrode may be estimated by the depth of colour induced. This electrochromic property is exploited in this invention by constructing a thin film cell 1 in which the sample array forms one electrode 2 and the electrochromic material the other electrode 3, that is the counter-electrode. Provided that the electrochromic counterelectrode 3 does not impede the current it will record the charge passed from each point on the electrocatalyst array forming electrode 2 as a colour modulated image. Between the electrodes 2 and 3 is the electrolyte solution 4.

Since the charge passed is the time integral of the current, the current is given by the rate of change of charge, as displayed by the rate of change of colour in the electrode. A series of snapshots of the electrode can be used to indicate the current-time profile as shown schematically in FIG. 3.

Figure 3:
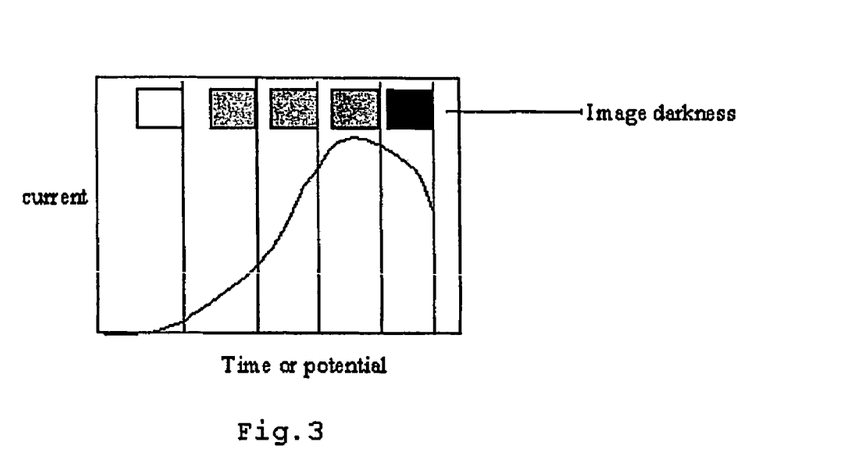
FIG. 3 shows the change of current with time, as estimated from the colour change of counter-electrode 3 of FIGS. 1 and 2.

Depending on the choice of electrochromic material, the range of charge measurement can vary from about 1 to 50 mC cm$^{-2}$ full scale. Typical current densities of interest range from less than 1 microamp cm$^{-2}$ to 100 mA cm$^{-2}$ or more. The range and resolution of the current measurement can be adjusted by changing the scan rate and the sensitivity of the electrochromic material; for example, current densities up to 1 mA cm$^{-2}$ would be measured effectively in a ten-second scan using an imaging electrode with 10 mC cm$^2$ full-scale response.

Figure 4:
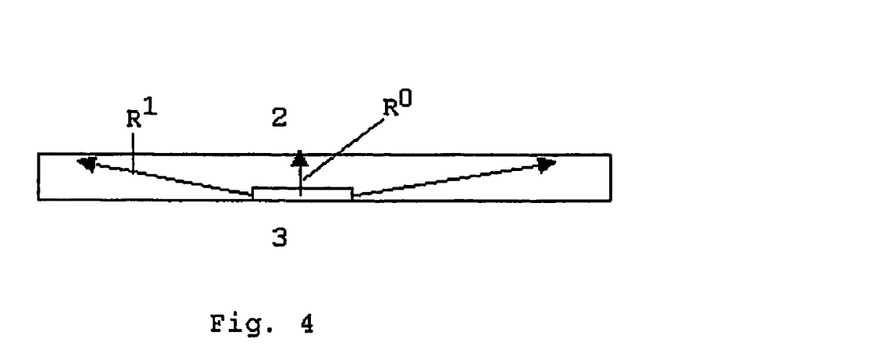
FIG. 4 is a diagrammatic side view of a test cell in accordance with the present invention.

In order to achieve the best results in accordance with the present invention, it is desirable to ensure that the dimensions of the cell are such as to obtain a good lateral resolution. This is because the image current spreads widely unless the lateral resistance of the electrolyte is made large by ensuring a relatively thin layer of solution of significant resistivity, as shown in FIG. 4 of the accompanying drawings. Provided that the resistance path, $R^1$, to a neighbouring region is large, the current is limited by a substantial Ohmic drop in the electrolyte. Preferably the resistance path $R^1$ is significantly greater than the reciprocal of the element area in square centimeters. An appropriate design of the electrolyte layer is required for a high resolution and a high density of array electrodes.

The electrochromic material forming part or all of the counter-electrode may be any such material which will change some property, preferably visual property, in response to the passage of current and in a manner proportional to the current passed. A suitable such material is tungsten oxide, and this is the preferred material for use in the present invention. However, other materials can be used, for example: inorganic compounds, such as described by C. G. Granqvist, "Handbook of Inorganic Electrochromic Materials", Elsevier (1995), (Amsterdam), ISBN 0444 89930 8; organic materials, such as viologens, metal phthalocyanines, conducting polymers such as polyaniline, polythiophenes, as described in P. M. S. Monk, R. J. Mortimer and D. R. Rosseinski, "Electrochromism, Fundamentals and Applications", VCH (1995), (Weinheim), ISBN 0-89573-788-4. Easily reduced, insoluble metal compounds such as silver halides could also be used, as reduction to the finely divided metal causes electrochromic change.

Where, as is the case with tungsten oxide, the electrochromic material does not possess sufficient mechanical strength to form an electrode alone, it is preferably supported by a suitable inert material. If it is desired to monitor the change in colour or intensity of colour as the experiment proceeds, it is preferred that the supporting material should be transparent or translucent, so that the change may be viewed from the side of the support which does not bear the electrochromic material. Furthermore, the support material is required to be electrically conducting to provide electrical contact to the electrochromic electrode. A suitable material for this is glass, coated with a transparent conducting film, such as indium tin oxide (ITO) or fluorine-doped tin oxide (FTO). Noble metals may also be used provided they do not catalyse the reaction studied.

Tungsten oxide changes its colour according to its oxidation state:

$$WO_3 + x(Li^+ + e^-) \rightarrow Li_x W^{VI}_{(1-x)} W^V_x O_3$$
(very pale yellow) (blue)

This is a readily observed change, which makes this particularly suitable for use as the electrochromic material.

The nature of the material to be tested in accordance with the present invention will, of course, depend upon its intended use. Where it is to be tested for its catalytic activity in a methanol fuel cell, it may be, for example, an alloy containing one of the platinum group metals, or any combination of elements which form a conducting film. For other uses, such as electrosynthesis, other materials may be tested according to the type of reaction to be catalysed.

Since the present invention allows a plurality of different materials to be tested at the same time, in the case of where the material being tested is on the first electrode, these materials are preferably supported on a suitable electrically conductive support material. The support may be inert, or may enhance the catalytic activity by increasing the accessible surface area or through a catalyst-support interaction. For most purposes, a carbon support will be recommended. A porous support may also be used, particularly where the reactant is a gas external to the cell, rather than dissolved in the electrolyte.

The nature of the electrolyte employed in the test cell of the present invention where the material being tested is on the first electrode may be important. It is preferred, in order to achieve the most accurate results, that the electrolyte should be as close as possible, and preferably identical to, the electrolyte to be used in the actual device, e.g. fuel cell, for which the material being tested is to be used; Where the material to be tested is to be tested for a catalytic effect, the electrolyte should contain some of the material whose reaction the test material is to catalyse.

The electrolyte may be a free liquid, for example an aqueous solution of acid, or the same contained within the pores of suitable porous separator or the same absorbed in a polymer or a solid electrolyte film as used in the intended fuel cell. The electrolyte should preferably be the same as that used in the fuel cell, although it may be diluted to increase the lateral resistance, improving lateral resolution as noted above. In the case of a methanol fuel cell, for example, a suitable electrolyte is sulphuric acid at a concentration of from 0.05 to 2 M, more preferably about 1 M. It should be noted that the term "electrolyte" as used herein means a substance which is an ionic conductor.

Where the material to be tested is the electrolyte, this will normally be a polymer electrolyte, e.g. an electrolyte gel formed of polyvinylidene fluoride copolymers, propylene carbonate and a lithium salt, or, in the case of a fuel cell electrolyte, a proton conducting polymer, such as Nafion (trade mark). In the former case, the proportions of the compounds making up the gel could be varied; in the latter case, different additives could be incorporated in the Nafion and their effects examined.

The test cell may be completed by a container, which should be made of a material inert to the electrolyte and anything in the electrolyte. Glass or various plastics are suitable. The test materials and counter-electrode are connected by suitable conductive means to a source of controllable current, as is well known in the art.

The invention is further illustrated by the following non-limiting Examples.

EXAMPLE 1

Figure 5:
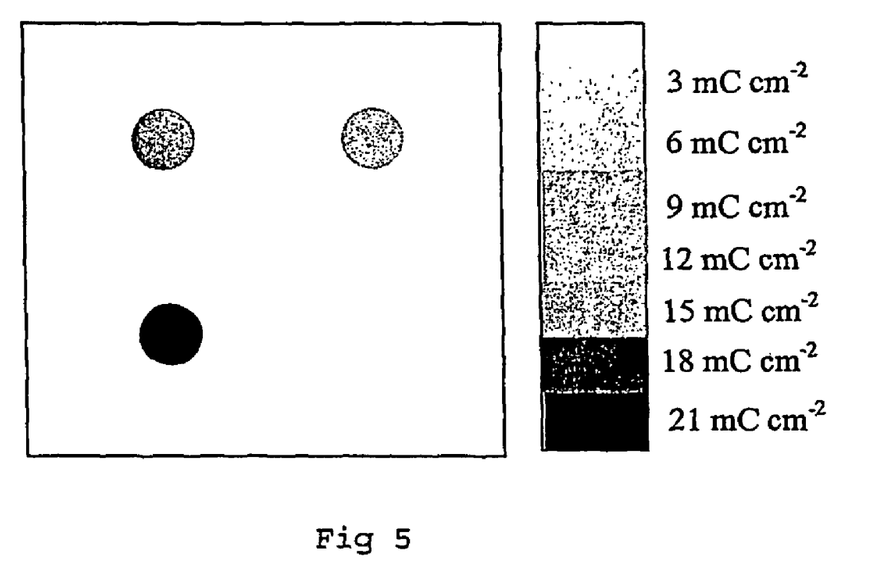
FIG. 5 shows the appearance of the counter-electrode and calibration strip obtained after carrying out the experiment described in the following Example 1.

A cell was constructed from the following components. The working electrode consisted of an array of four equally-sized discs of candidate platinum-containing catalytic electrodes of differing compositions placed on a conducting carbon substrate, 4 cm square deposited on a 4 cm square of transparent fluorine-doped tin oxide coated glass with a conductivity of less than 50 Ohms per square. The electrolyte was a 1 M solution of methanol in 0.5 M aqueous sulphuric acid absorbed in a Whatman 500 filter paper. The two electrodes were pressed together against the filter paper to form the cell. The cell was connected to a potentiostat and the potential at the carbon electrode with respect to the coated glass electrode was scanned linearly from zero to 0.5 volts in three seconds while the counterelectrode was photographed at 0.3 second intervals with a digital camera. A duplicate sample of the tungsten oxide electrode was subjected to galvanostatic cathodic treatment while being immersed stepwise in an electrolyte containing 0.5 M sulphuric acid. The time for each step was controlled to give charge increments of 3, 6, 9, 12, 15, 18 and 21 mC cm$^{-2}$ in bands along the electrode to serve as a calibration strip. This electrode was then photographed under the same light conditions as the screening experiment. The results are shown schematically in FIG. 5.

Figure 6:
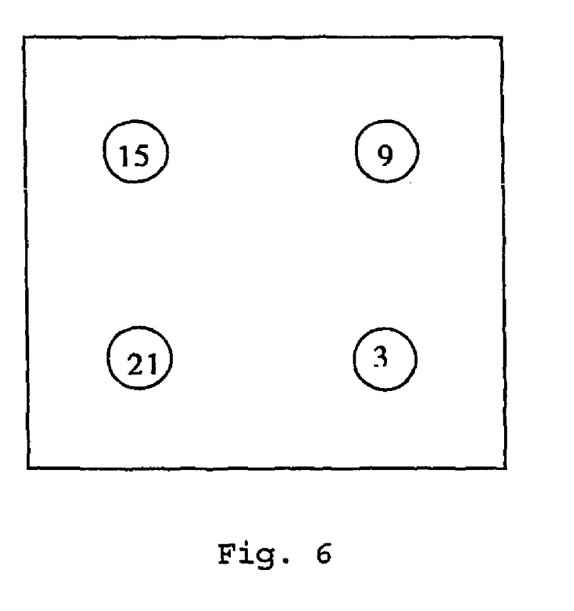
FIG. 6 illustrates the result of the computation of the charge passed through each region of the counter-electrode of FIG. 5 using the calibration strip.

From the results above it was concluded that the most promising catalyst for methanol oxidation was the one placed at the bottom left position as shown in FIG. 6.

EXAMPLE 2

An array of nine catalyst spots was deposited on a gold/chromium coated glass microscope slide as follows. A platinum catalyst supported on carbon was dispersed in acetic acid solution. Three spots, approximately 3 mm diameter, of the dispersion were placed in a row on the glass, each containing three, two and one drop respectively of the dispersion. A second and third row of spots were placed underneath using an identical procedure to the first row. Approximately 2 µl of Nafion (trade mark) dispersed in aqueous ethanol was placed on each spot before drying the array with a warm air gun. The array was used as one electrode of in a cell separated with two filter paper spacers soaked with an electrolyte consisting of 0.001 M $H_2SO_4$ containing 2 M methanol. The counterelectrode was a layer of about 300 nm tungsten oxide on transparent fluorine-doped tin oxide coated glass with a conductivity of less than 50 Ohms per square. A silver/silver oxide wire reference electrode was placed in contact with the filter paper at one end of the array. A potentiostat was used to control the potential between the catalyst array and the reference electrode by passing an appropriate current into the tungsten oxide electrode. The potential was scanned at 20 mVs$^{-1}$ from –0.2 V to 1.0 V.

Figure 7:
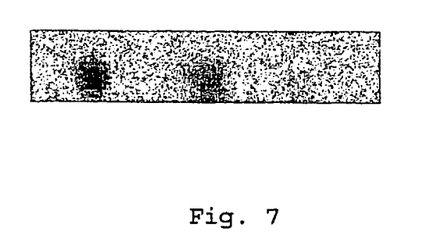
FIG. 7 shows a photograph of the centre portion of a counter-electrode prepared and processed according to Example 2 below. Three dark regions correspond to the areas opposite active catalyst regions on the first electrode.
Figure 8:
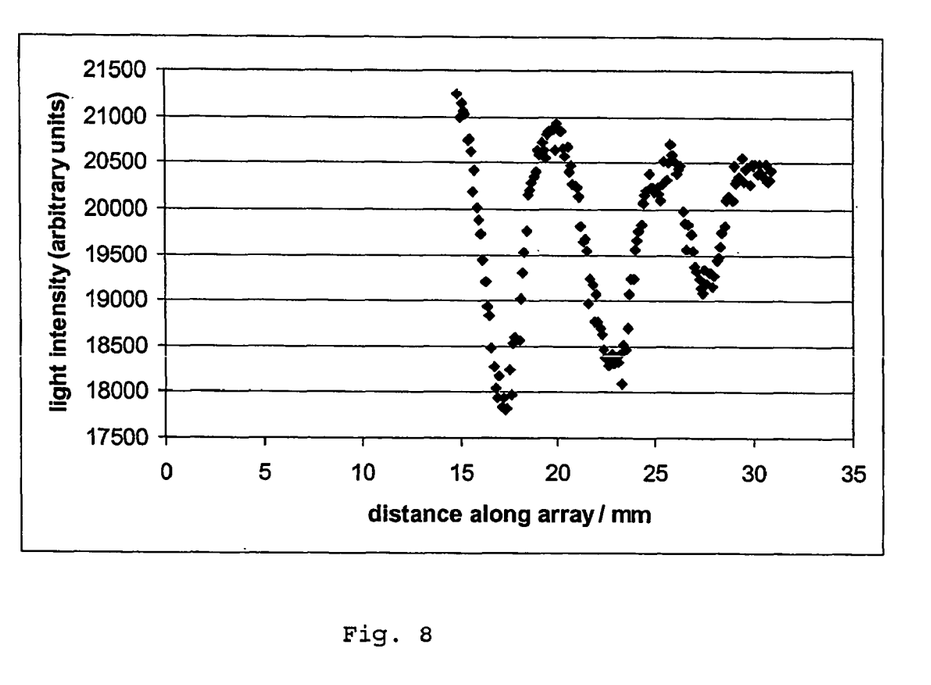
FIG. 8 shows the profile of optical intensity at the 600 nm wavelength across the counter-electrode of FIG. 7 illuminated under normal laboratory lighting.

The counterelectrode was observed using an Andor Technology DV437 front illuminated frame transfer CCD camera cooled to –50° C. with a macro lens (fl 15 cm) and a 600 nm band pass filter. The total substrate window imaged was 55 mm×20 mm. The intensity data measured was the total e-count for each pixel during the capture. Each image in the kinetic series was an on-chip accumulation of 5 exposures before readout. Each exposure was for 9 ms and each image took 1.8 s in total (0.3 s delay between exposures). One image was taken every 5 s thereafter to a total of 10 images during the 60 s scan. FIG. 7 shows the image of the central row of three spots after 6 s and at a potential of –0.16 V with respect to the reference electrode. The gradation in optical density is quantified in FIG. 8. The charge passed at each spot was calculated from a calibration curve of the optical density as a function of charge density.

EXAMPLE 3

A cell array was constructed from the following components.

A working electrode array consisted of 64 equally-sized glassy carbon 3 mm diameter cylinders supported in a glass-filled PTFE (polytetrafluoroethylene) plate. Each cylinder was coated with a platinum catalyst prepared as follows. The catalyst stock solution (12.2 mg of platinum black in 1 ml solution consisting of 95 wt % acetic acid and 5 wt % Nafion solution) was sonicated for 2 hours immediately prior to deposition and as aliquots were removed and deposited onto the cylinders. The array was then allowed to air dry for 3 hours before use. Each cylinder had a specified mass loading of platinum of 6, 12, 18 or 18 μg according to the pattern shown in FIG. 9a.

The array was covered with a Whatman Glass Microfibre filter (GF/F grade) as a separator soaked with an aqueous solution containing 1 M methanol and 1 mM sulphuric acid.

The electrochromic counterelectrode consisted of a layer of 300 nm tungsten oxide on transparent fluorine-doped tin oxide coated glass with a conductivity of less than 50 Ohms per square. The electrode was pre-conditioned by placing it as a working electrode into a cell containing 0.1 M sulphuric acid as the electrolyte, a platinum counterelectrode and SCE reference electrode. The electrode was cycled 10 times between its open circuit rest potential and −200 mV vs SCE, finally leaving at −50 mV for 10 minutes before washing with distilled water and transferring to the array cell covering the separator.

The electrochromic counterelectrode was observed using a Starlight Xpress SXV-H9CCD camera with a normal 35 mm lens adapted using an additional 28 mm tube spacer between the lens and camera to give a macro effect and a 645 nm band pass filter.

The cell was connected to a potentiostat capable of holding the potential of each element in the array at a fixed value with respect to the electrochromic counterelectrode by supplying a measured current to each element.

The working electrode array was initially held at zero volts versus the counterelectrode then switched to +0.4 V while taking readings of the current at each individual element as a function of time up to 40 s. The digital camera was used to provide a simultaneous record of the absorbance of the counterelectrode during the course of the experiment.

Figure 9:
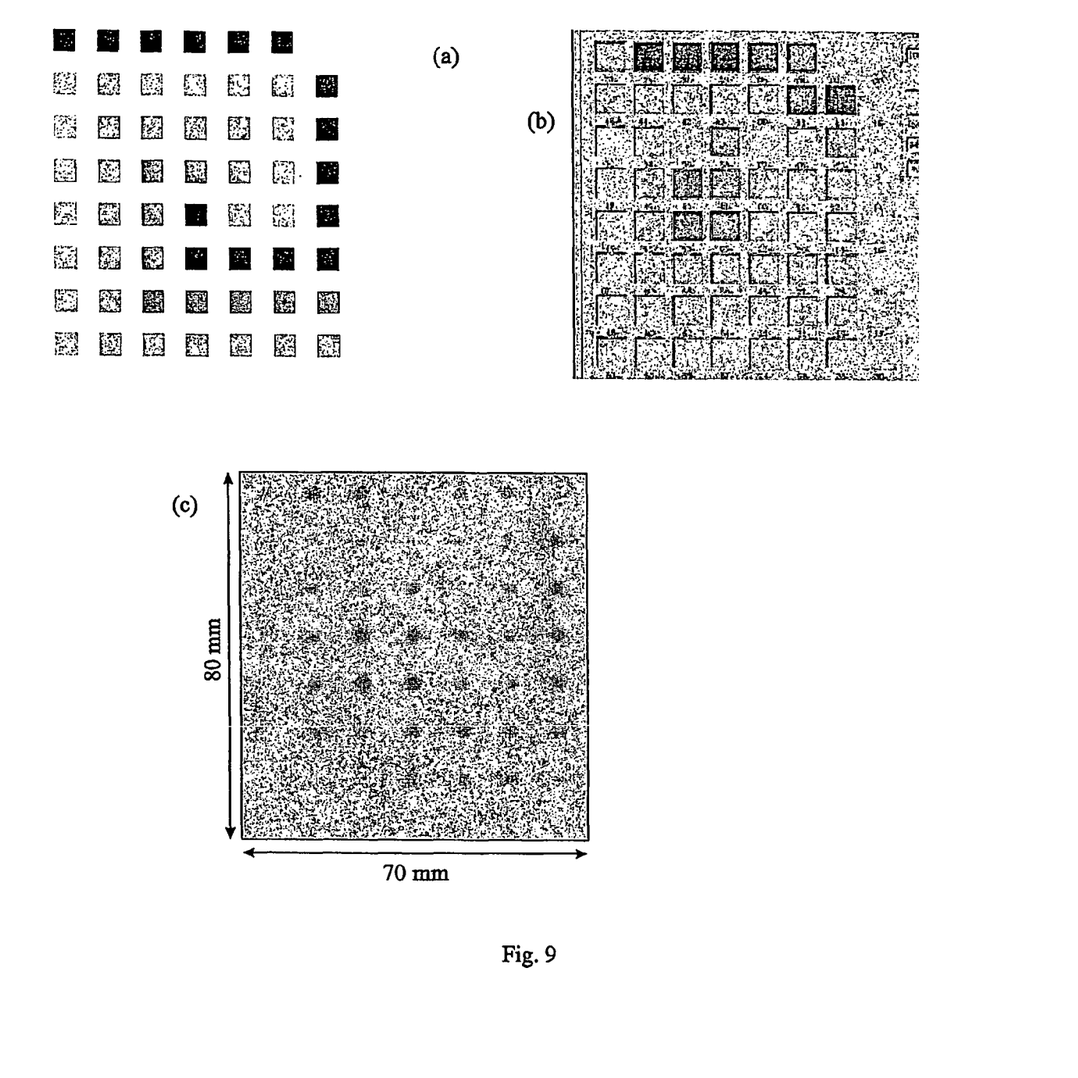
FIG. 9a shows the mass loading of platinum on an electrode in Example 3.
FIG. 9b shows the total charge passed at each element during the experiment of Example 3.
FIG. 9c shows the indicator action of the electrochromic counterelectrode in Example 3.

The total charge passed at each element during the experiment is illustrated in FIG. 9b. The pattern verifies that the catalyst activities, indicated by the darkest spots, were distributed as intended according to the pattern of FIG. 9a.

FIG. 9c shows the indicator action of the electrochromic counterelectrode. The pattern of spots gives at least a qualitative correlation with the pattern of FIG. 9b, identifying the most active catalysts as the darkest spots.

EXAMPLE 4

A cell array was constructed which was similar to that of Example 3, except that it contained only four elements, with 40 wt. % platinum on carbon catalyst loadings of 5.7, 11.4, 17.1 and 22.8 μg respectively.

Figure 10:
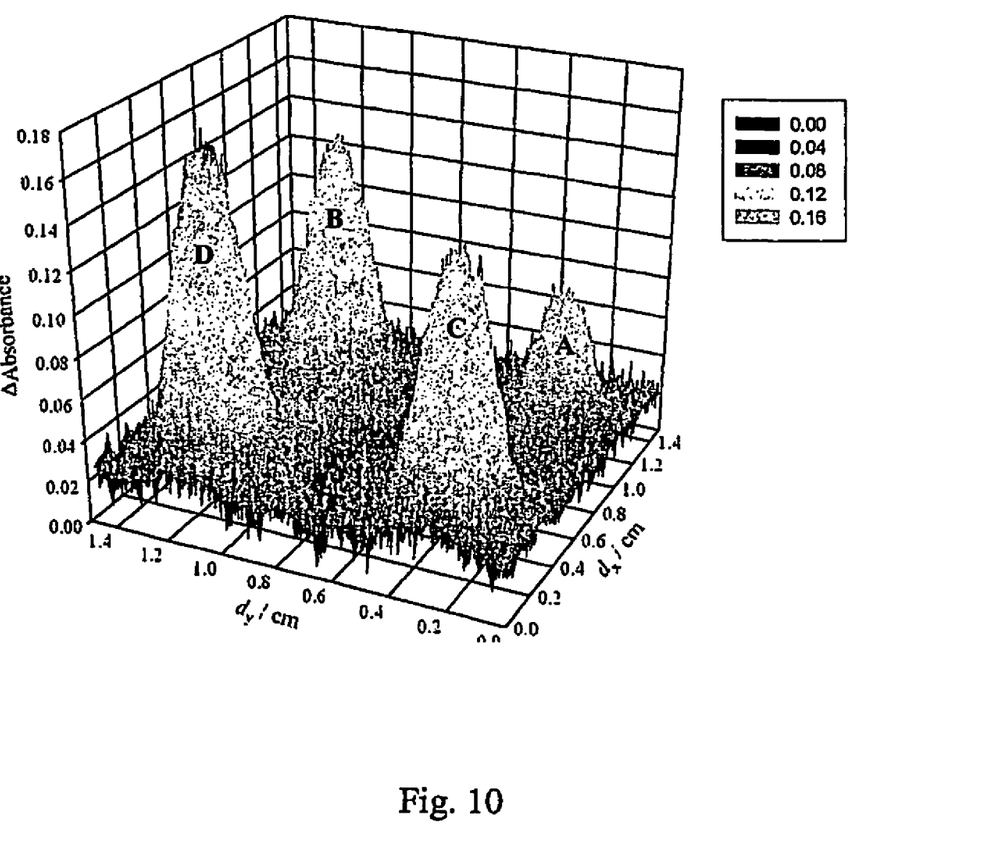
FIG. 10 shows the total charge passed is shown as a function of the image position in Example 4.

The array was subjected to a potential step from zero to +0.4 V versus the counterelectrode as before and the currents were measured as a function of time while the counterelectrode plate was photographed to obtain the absorbance as a function of position along the electrode. FIG. 10 shows a 3-dimensional representation of the optical density map for the four spots developed opposite the catalyst samples.

Figure 11:
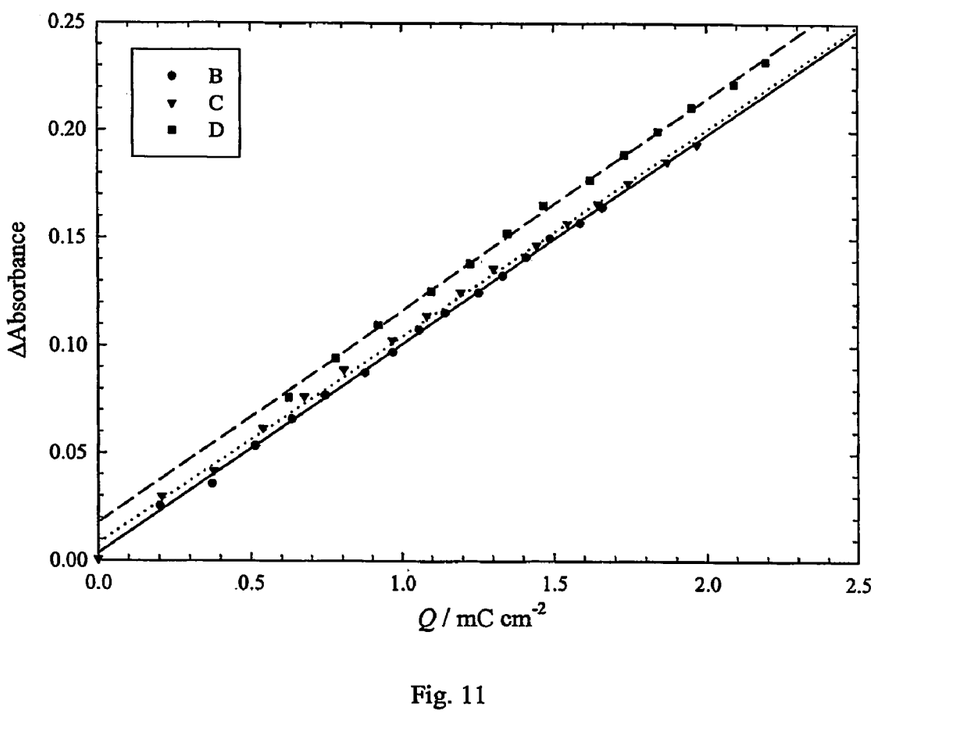
FIG. 11 shows the charges recorded during Example 4, plotted against the absorbance at corresponding times recorded on the image of the centre of each counterelectrode position opposite the catalyst samples.

The charges recorded at various times during the experiment are plotted in FIG. 11 against the absorbance at corresponding times recorded on the image of the centre of each counterelectrode position opposite the catalyst samples. It may be seen that there is a quantitative and linear relation between the optical absorbance and the charge passed. Therefore the optical density map of FIG. 10 can be taken to be a representation of the total charge passed as a function of position.

EXAMPLE 5

Figure 12:
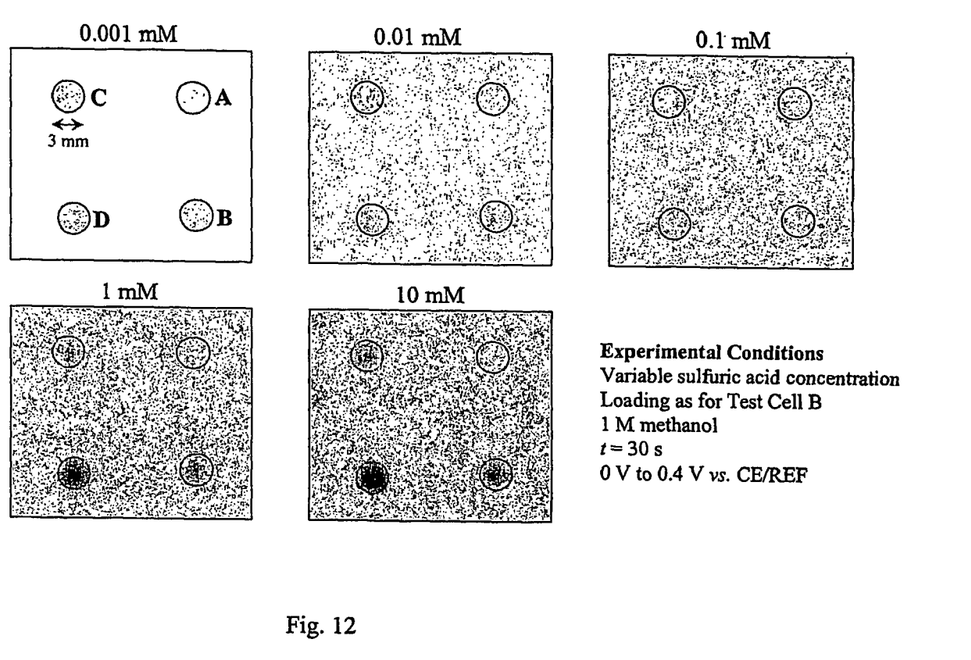
FIG. 12 shows pictures of the electrochromic electrodes of Example 5.

The experiment of Example 4 was repeated several times with fresh, preconditioned electrochromic counterelectrodes, each time using a different concentration of sulphuric acid in the electrolyte but with the same methanol concentration and catalyst loadings in each case. The results are shown in FIG. 12 for the five concentrations used. At the higher concentrations, the spots appear on a variable background, whereas at the low electrolyte concentration the background is almost unchanged from the initial material as it appeared before the potential step. The experiment illustrates the effect of using a low concentration of electrolyte.

The invention claimed is:

1. An electrochemical cell comprising a plurality of samples of material for testing electrocatalytic behavior of a plurality of materials, said cell comprising:
   a first electrode bearing the plurality of samples of material to be tested;
   a counter-electrode bearing an electrochromic material whose reflection, refraction or absorption of electromagnetic energy changes in a manner proportional to the total charge passed through it; and
   an electrolyte between and in electrical contact with the first electrode and the counter-electrode;
   wherein said first electrode comprises a plurality of regions, each region bearing a sample of material to be tested, the regions being electrically connected to a common terminal, and
   wherein the sample of material to be tested is an electrocatalyst, and the electrolyte contains the material whose reaction is to be catalyzed by said electrocatalyst,
   wherein said reaction changes the total charge passing through the counter-electrode bearing the electrochromic material, and the changes in reflection, refraction or absorption of electromagnetic energy of the electrochromic material with respect to each region of electrocatalyst is indicative of the electrocatalytic activity of each sample of the electrocatalyst on said first electrode on the reaction of the material to be catalyzed by the electrocatalyst of the electrolyte.

2. An electrochemical cell according to claim 1 in which the electrochromic material is tungsten oxide.

3. An electrochemical cell according to claim 1 in which a reference electrode is contacted with the electrolyte for potential measurement and control.

4. An electrochemical cell according to claim 1 wherein the first electrode comprises an electrically conductive substrate, and the sample materials are supported on the electrically conductive substrate.

* * * * *